US00PP29026P2

(12) United States Plant Patent
O'Connell

(10) Patent No.: US PP29,026 P2
(45) Date of Patent: Feb. 27, 2018

(54) ***AEONIUM* PLANT NAMED 'CARIBBEAN ROSE'**

(50) Latin Name: ***Aeonium* hybrid**
Varietal Denomination: Caribbean Rose

(71) Applicant: Renee O'Connell, Escondido, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/330,714

(22) Filed: Oct. 27, 2016

(51) Int. Cl.
*A01H 5/12* (2006.01)

(52) U.S. Cl.
USPC ..... Plt./373

(58) Field of Classification Search
USPC ..... Plt./373
CPC ..... A01H 5/00; A01H 5/02
See application file for complete search history.

*Primary Examiner* — June Hwu
(74) *Attorney, Agent, or Firm* — Cassandra Bright

(57) ABSTRACT

A new and distinct *Aeonium* cultivar named 'Caribbean Rose' is disclosed, characterized by compact clusters of lime green rosettes, foliage with a very thin apical blush colored pink. Plants grow quickly, forming offsets at a distinctively young age. Due to abundant and early offsetting, plants can be produced commercially in various pot sizes, from 9 cm to 2 gallon, while maintaining an attractive compact habit. Foliage resists edema seen in some *Aeonium* cultivars and plants are observed tolerant to temperatures as high as 100 degrees Fahrenheit. *Aeonium* is, typically produced as a container plant for the patio or for landscape use.

1 Drawing Sheet

Latin name of the genus and species: *Aeonium* hybrid.
Variety denomination: 'CARIBBEAN ROSE'.

BACKGROUND OF THE INVENTION

The new cultivar, *Aeonium* 'Caribbean Rose', was found by the inventor, Renee O'Connell, as the result of a crossing made February 2011 as part of a planned breeding program. The seed parent variety is the unpatented proprietary variety referred to as *Aeonium* hybrid 'Menthe 11. The pollen parent is the unpatented variety *Aeonium* hybrid 'LP II'. *Aeonium* 'Caribbean Rose' was selected by the inventor, Renee O Connell, in September of 2012 from a group of seedlings resulting from the 2011 crossing, at a commercial greenhouse in Vista. Calif.

Asexual reproduction of the new cultivar 'Caribbean Rose' was first performed in Vista, Calif., at a commercial greenhouse, by vegetative off-sets in October of 2013. 'Caribbean Rose' has since produced multiple generations and has shown that the unique features of this cultivar are stable and reproduced true to type.

SUMMARY OF THE INVENTION

The cultivar 'CARIBBEAN ROSE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CARIBBEAN ROSE' These characteristics in combination distinguish 'CARIBBEAN ROSE' as a new and distinct *Aeonium* cultivar:

1 *Aeonium* 'Caribbean Rose' exhibits compact clusters of lime green rosettes, with a very thin pink apical blush.

2. *Aeonium* 'Caribbean Rose' grows quickly, and begins to form clusters at a young size, often first offsetting in a 4" pot.
3. *Aeonium* 'Caribbean Rose' can be grown in pot sizes from 9 cm to 2 gallon due to its early offsetting, while maintaining its compact habit.
4. The rosettes of *Aeonium* 'Caribbean Rose' do not exhibit the tendency towards the physiological "edema"(scars or scabs) that many other lineages involving *Aeonium*, especially those of nobile lineage exhibit.
5. *Aeonium* 'Caribbean Rose' has been trialed in the landscape in full sun in Escondido, Calif., and has shown good tolerance to the summer heat to 100 degrees Fahrenheit.

Plants of the new cultivar 'CARIBBEAN ROSE' are similar to plants of the seed parent in most horticultural characteristics, however, plants of the new cultivar 'CARIBBEAN ROSE' differ in the following;

1. *Aeonium* 'Caribbean Rose' exhibits a more rounded morphology than does *Aeonium* 'Menthe 11'.
2. *Aeonium* 'Caribbean Rose' is freely offsetting, whereas *Aeonium* 'Menthe 11' only produces occasional offsets.
3 *Aeonium* 'Caribbean Rose' exhibits a faster growth rate than *Aeonium* 'Menthe 11'.
4. *Aeonium* 'Caribbean Rose' is freely offsetting from an early size and age, whereas *Aeonium* 'Menthe 11' offsets sparsely, and at a larger size.
5. *Aeonium* 'Caribbean Rose' forms a more compact morphology than does *Aeonium* 'Menthe 11'.

Plants of the new cultivar 'CARIBBEAN ROSE' are similar to plants of the pollen parent in most horticultural characteristics, however, plants of the new cultivar 'CARIBBEAN ROSE' differ in the following;

1 *Aeonium* 'Caribbean Rose' does not exhibit the tendency towards physiological "edema" that is exhibited by *Aeonium* 'LP II'.

2. *Aeonium* 'Caribbean Rose' forms larger rosettes than does *Aeonium* 'LP II'.
3. *Aeonium* 'Caribbean Rose' forms rosettes with a more globular morphology than the rosettes of *Aeonium* 'LP II'.
4. *Aeonium* 'Caribbean Rose', due to the larger rosettes, and more upright overall morphology, is more suitable for larger pot sizes, such as 8 inch and 2 gallon, than is *Aeonium* 'LP II'.

COMMERCIAL COMPARISON

Plants of the new cultivar 'CARIBBEAN ROSE' are comparable to the unpatented, commercial variety *Aeonium* 'Lily Pad'. The two *Aeonium* varieties are similar in most horticultural characteristics; however, the new variety 'CARIBBEAN ROSE' differs in the following:

1. *Aeonium* 'Caribbean Rose' quickly forms clusters of somewhat spherical rosettes whereas as *Aeonium* 'Lily Pad' produces clusters of more flattened rosettes.
2. *Aeonium* 'Caribbean Rose' does not exhibit the tendency to physiological "edema" that *Aeonium* 'Lily Pad' suffers.
3. *Aeonium* 'Caribbean Rose' has exhibited much more tolerance to summer heat and seasonal rosette closure than does *Aeonium* 'Lily Pad'.

Plants of the new cultivar 'CARIBBEAN ROSE' can also be comparable to the unpatented commercial variety *Aeonium* 'Party Platter'. The two *Aeonium* varieties are similar in most horticultural characteristics; however, the new variety 'CARIBBEAN ROSE' differs in the following:

1. *Aeonium* 'Caribbean Rose' produces more spherical rosettes, whereas the rosettes of *Aeonium* 'Party Platter' are generally flattened, growing taller by virtue of stem offsetting pushing the central rosette upward.
2. *Aeonium* 'Caribbean Rose' exhibits more sun tolerance than does *Aeonium* 'Party Platter', which does best with a shade exposure.
3 *Aeonium* 'Caribbean Rose' due to its spherical rosette morphology, exhibits more resistance to disease than does *Aeonium* 'Party Platter', which, because of its flatter rosette morphology, tends to "trap' water in its apical meristem, often leading to apical rot.
4. *Aeonium* 'Caribbean Rose' has exhibited more heat and full tolerance, particularly in the hot summer, than *Aeonium* 'Party Platter'.

BRIEF DESCRIPTION OF THE PHOTOGRAPH

The accompanying photograph illustrates in full color a typical of plant of *Aeonium* 'Caribbean Rose' grown in a shadehouse in Vista, Calif. at a light intensity of approximately 2000 to 3000 fc. Age of the plant photographed is approximately 10 months from a rooted plantlet.

The photograph was taken using conventional techniques and although colors may appear different from actual colors due to light reflectance it is as accurate as possible by conventional photographic techniques. All photographs provided by the breeder.

DETAILED BOTANICAL DESCRIPTION

In the following description, color references are made to The Royal Horticultural Society Colour Chart, 2007, except where general terms of ordinary dictionary significance are used. The following observations and measurements describe 'Caribbean Rose' plants in a commercial shadehouse in Vista, Calif. Temperatures ranged from approximately 6° C. to 35° C. night and day. No artificial light, photoperiodic treatments or chemical treatments were given to the plants. Natural light conditions were approximately 4000 fc of light. Measurements and numerical values represent averages of typical plant types.

Botanical classification: *Aeonium* hybrid 'CARIBBEAN ROSE'.

PROPAGATION

Type of propagation typically used: Vegetative offsets.

Time to initiate roots: About 18 days at approximately 24° C.

Root description: Fibrous, brown, not accurately measured with a color chart.

PLANT

Age of plant described: Approximately 4 months.

Container size of the plant described: 6 inch.

Growth habit: Upright, caulescent, with a terminal rosette, freely offsetting from below rosette and between leaves of the rosette to produce cluster.

Height: Approximately 13 cm to top of highest leaf.

Plant spread: 23 cm.

Growth rate: Moderately fast.

Branching characteristics: Freely offsetting.

Rosettes per plant: Average range 12 to 20.

FOLIAGE

Leaf:

*Arrangement*.—Rosulate.

*Average length*.—Approximately 6 cm.

*Longest length*.—Approximately 7.0 cm.

*Average width*.—3.2 cm.

*Widest width*.—Approximately 4.0 cm.

*Width at base*.—1.1 cm.

*Shape of blade*.—Spatulate.

*Apex*.—Mucronate.

*Base*.—Cuneate.

*Margin*.—Finely ciliate.

*Texture of top surface*.—Glabrous.

*Texture of bottom surface*.—Glabrous.

*Quantity of leaves per rosette*.—Average range 35 to 50.

*Color*.—Young foliage upper side: Near RHS Green 137C. Base Yellow-Green 144D, White 155A at attachment. Young foliage, under side: Near RHS Green 137C. Base Yellow-Green 144D, White 155A at attachment. Mature foliage upper side: Near RHS Green 143A. Base Yellow-Green 144D. Apical margin has a very fine flush near Red-Purple 59A. Mature foliage, under side: Near RHS Green 143A. Base Yellow-Green 144D. Apical margin has a very fine flush near Red-Purple 59A.

*Venation*.—There is no visual appearance of venation.

FLOWER

Flowering not observed to date.

REPRODUCTIVE ORGANS

Flowering not observed to date.

OTHER CHARACTERISTICS

Fruits and seeds: Plant has not flowered or produced fruits and seeds to date.

Temperature tolerance: Tolerates temperatures from approximately −2 degrees C. to 40 degrees C.

Disease/pest resistance: Displays the same disease and pest resistance of any other comparable *Aeonium*.

Drought tolerance: Tolerates at least 3 weeks of high temperatures without supplemental water, showing no serious damage to plant.

What is claimed is:

1. A new and distinct cultivar of *Aeonium* plant named 'CARIBBEAN ROSE' as herein illustrated and described.

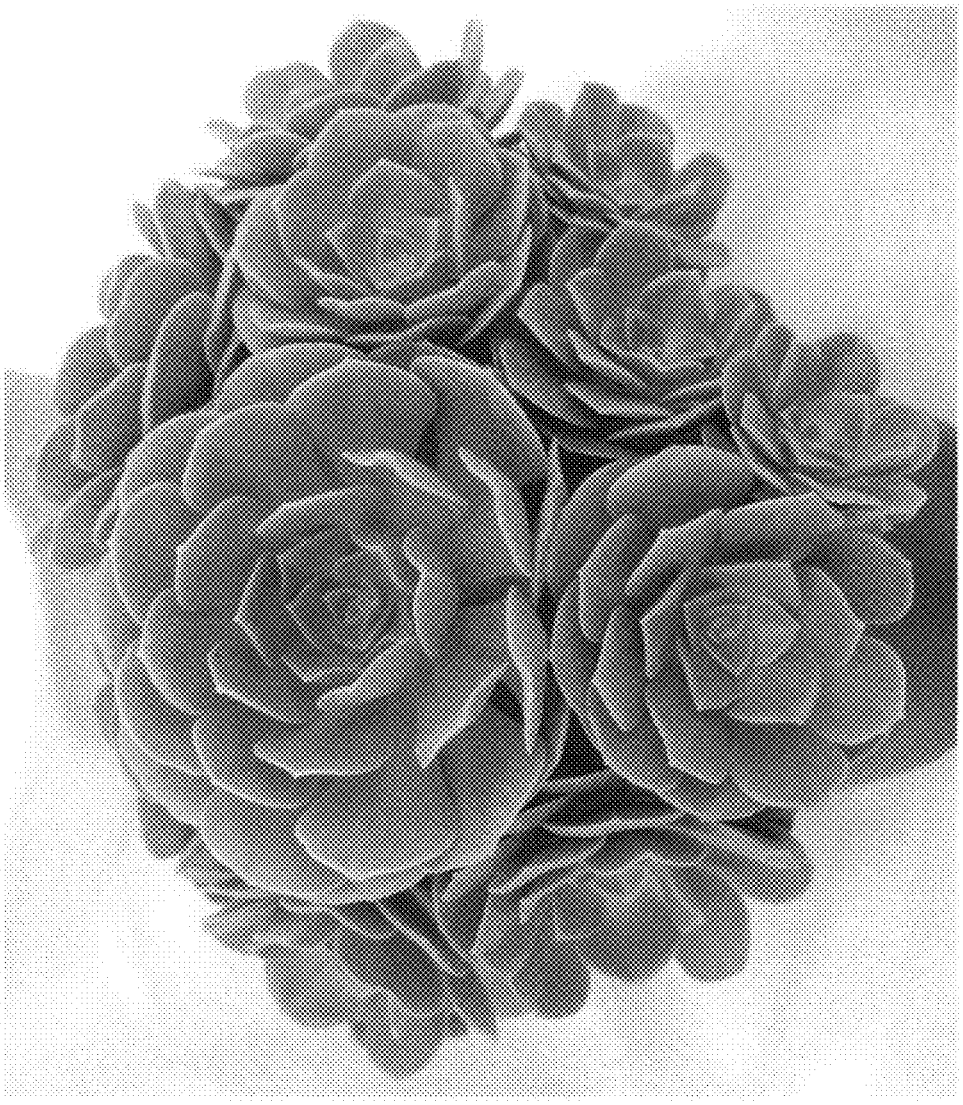

* * * * *